United States Patent [19]

Sturm

[11] 4,402,963
[45] Sep. 6, 1983

[54] MICROBICIDAL DIOXOLANYLALKYLTRIAZOLE COMPOSITIONS

[75] Inventor: Elmar Sturm, Aesch, Switzerland

[73] Assignee: Ciba-Geigy Corporation, Ardsley, N.Y.

[21] Appl. No.: 327,880

[22] Filed: Dec. 7, 1981

[30] Foreign Application Priority Data

Dec. 10, 1980 [CH] Switzerland ............ 9102/80

[51] Int. Cl.³ .......... A01N 43/64; C07D 405/06; C07D 405/14
[52] U.S. Cl. .................. 424/269; 424/245; 548/101; 548/262; 549/455
[58] Field of Search ........... 548/101, 262; 424/245, 424/269

[56] References Cited

U.S. PATENT DOCUMENTS

| | | | |
|---|---|---|---|
| 4,079,143 | 3/1978 | Balasubramanyan et al. | 548/262 |
| 4,259,505 | 3/1981 | Sturm et al. | 548/262 |
| 4,312,880 | 1/1982 | Draber et al. | 424/273 R |
| 4,338,327 | 7/1982 | Heeres et al. | 548/262 |

FOREIGN PATENT DOCUMENTS 1464224 2/1977 United Kingdom ............ 548/262

*Primary Examiner*—Alton D. Rollins
*Attorney, Agent, or Firm*—Frederick H. Rabin

[57] ABSTRACT

There are described novel compounds of the formula I defined herein

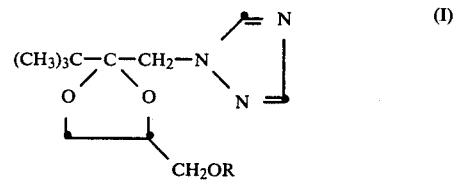

wherein R is a phenyl group which is unsubstituted or mono- to tetra-substituted by $C_1$-$C_4$-alkyl, halogen, nitro, cyano, trifluoromethyl, phenyl or $C_1$-$C_3$-alkoxy, or it is 3,4-methylenedioxy-phenyl, including the acid addition salts thereof with organic and inorganic acids as well as metal complexes thereof, all having tolerance to cultivated plants and possessing valuable microbicidal properties. They can be used for combating phytopathogenic microorganisms, particularly phytopathogenic fungi. The compounds of the formula I have for practical purposes a very favorable curative, systemic and preventive action for the protection of cultivated plants, without these being impaired as a result of undesirable side-effects. They can be used in practice on their own or in the form of microbicidal compositions.

13 Claims, No Drawings

MICROBICIDAL DIOXOLANYLALKYLTRIAZOLE COMPOSITIONS

The present invention relates to substituted 2-tert-butyl-2-(1H-1,2,4-triazolyl-methyl)-4-oxymethyl-1,3-dioxolanes of the formula I, to salts thereof with inorganic or organic acids and to metal complexes thereof, all having tolerance to cultivated plants, to the production of such compounds, to microbicidal compositions containing the compounds of the formula I as active ingredients, and to the use of compounds of the formula I for combating plant diseases.

The compounds embraced herein are compounds of the formula I

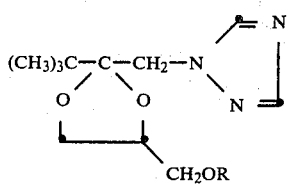

wherein R is a phenyl group which is unsubstituted or mono- to tetra-substituted by $C_1$-$C_4$-alkyl, halogen, nitro, cyano, trifluoromethyl, phenyl or $C_1$-$C_3$-alkoxy, or it is 3,4-methylenedioxy-phenyl, including the acid addition salts thereof with organic and inorganic acids as well as metal complexes thereof, all having tolerance to cultivated plants.

By alkyl or by alkyl moiety of another substituent are meant, depending on the given number of carbon atoms, for example the following groups: methyl, ethyl, propyl or butyl, as well as isomers thereof, such as isopropyl, isobutyl, sec-butyl or tert-butyl. Halogen in the present case is fluorine, chlorine, bromine or iodine, preferably fluorine, chlorine or bromine.

Examples of inorganic acids are: hydrochloric acid, hydrobromic acid, hydriodic acid, sulfuric acid, phosphoric acid, phosphorous acid and nitric acid.

Examples of organic acids are: trifluoroacetic acid, trichloroacetic acid, benzenesulfonic acid and methanesulfonic acid.

Metal complexes of the formula I consist of the basic organic molecule and an inorganic or organic metal salt, for example the halides, nitrates, sulfates, phosphates, tartrates, and so forth, of copper, manganese, iron, zinc and other metals. The metal cations can be present here in the various valencies in which they occur.

Compounds of the formula I exhibit a very valuable microbicidal spectrum. They can be used for example against phytopathogenic microorganisms, especially against phytopathogenic fungi.

The following individual compounds are particularly preferred:

(a) 2-tert-butyl-2-(1H-1,2,4-triazol-1-yl)-methyl-4-(2,4-dichlorophenoxy)-methyl-1,3-dioxolane, including the acid addition salts and metal complexes thereof;

(b) 2-tert-butyl-2-(1H-1,2,4-triazol-1-yl)-methyl-4-(3-trifluoromethyl-phenoxy)-methyl-1,3-dioxolane, including the acid addition salts and metal complexes thereof;

(c) 2-tert-butyl-2-(1H-1,2,4-triazol-1-yl)-methyl-4-(4-chlorophenoxy)-methyl-1,3-dioxolane, including the acid addition salts and metal complexes thereof; and (d) 2-tert-butyl-2-(1H-1,2,4-triazol-1-yl)-methyl-4-(3,4-dichlorophenoxy)-methyl-1,3-dioxolane, including the acid addition salts and metal complexes thereof.

The compounds of the formula I can be produced as described in the following.

Ketals of the formula I can be produced by reaction of a triazole of the formula II

wherein Me is hydrogen or preferably a metal atom, in particular an alkali metal atom, with a compound of the formula III

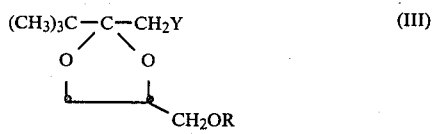

wherein R has the meanings defined under the formula I, and Y is one of the customary removable groups, for example halogen, especially chlorine, bromine or iodine, or the benzenesulfonyloxy, p-tosyloxy, trifluoroacetyloxy or, preferably, lower alkylsulfonyloxy group, such as the mesyloxy group.

The reaction of II with III is preferably performed in a relatively polar organic solvent inert however to the reactants, for example N,N-dimethylformamide, N,N-dimethylacetamide, dimethyl sulfoxide, acetonitrile, hexamethylphosphoric acid triamide, and the like. Such solvents can be used in combination with other solvents inert to the reactants, such as aliphatic or aromatic hydrocarbons, for example benzene, toluene, xylene, hexane, petroleum ether, chlorobenzene, nitrobenzene, and so forth.

Alkali iodide (such as NaJ or KJ) can advantageously be used to accelerate the reaction when Y is chlorine or bromine. Elevated temperatures of 0° to 220° C., preferably 80°–170° C., are of advantage, and the reaction mixture is advantageously refluxed.

When Me in the formula (II) is hydrogen, the process is performed in the presence of a base. Examples of suitable bases are inorganic bases such as oxides, hydroxides, hydrides, carbonates and hydrogen carbonates of alkali metals and alkaline-earth metals, as well as tert-amines, such as triethylamine, triethylenediamine, pyridine, 4-dimethylaminopyridine, 4-pyrrolidylpyridine, and so forth, or piperidine.

In this production process, the end product of the formula I can be isolated from the reaction medium and, if required, then purified by one of the customary methods, for example by extraction, crystallisation, chromatography, distillation, and the like.

The starting ketals of the formula III can be obtained for example from the basic ketone of the formula IV

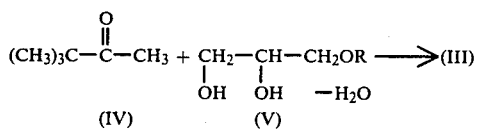

$$-H_2O$$

by reaction with the diol of the formula V in an inert solvent, for example in a halogenated hydrocarbon (such as methylene chloride, ethylene chloride, chloroform, carbon tetrachloride, and so forth) and simultaneous or subsequent halogenation; or by reaction of the ketone VI

wherein Y has the meaning given under the formula III, with the diol V in an inert solvent. An addition of p-toluenesulfonic acid is advantageous for accelerating both reactions.

These ketalisation reactions can be performed analogously to ketalisation reactions already known, for example by a process analogous to that for the production of 2-bromomethyl-2,4-diphenyl-1,3-dioxolane [Synthesis, 1974 (I), 23].

The preferred method of carrying out the ketalisation reaction comprises refluxing both reactants for several hours, together with an azeotrope-former, in one of the customary organic solvents. Suitable azeotrope-formers are for example: benzene, toluene, xylene, chloroform or carbon tetrachloride. The reaction is performed for example in the presence of a simple alcohol, such as ethanol, propanol, butanol, pentanol, and the like; and an addition of a strong acid, for example p-toluenesulfonic acid, can be advantageous for accelerating the reaction. Applicable organic solvents in this case are for example aromatic hydrocarbons, such as benzene, toluene, xylene, and so forth, and saturated hydrocarbons, such as n-hexane.

The production process described forms a part of the subject matter of the present invention.

In the described ketalisation reactions of a ketone with a substituted α,β-diol, it is possible for mixtures of diastereoisomers of the resulting ketal to be formed. Correspondingly, diastereoisomeric mixtures of the final products I are in general formed from the starting ketones. The compounds of the formula I can be in the following two diastereoisomeric forms:

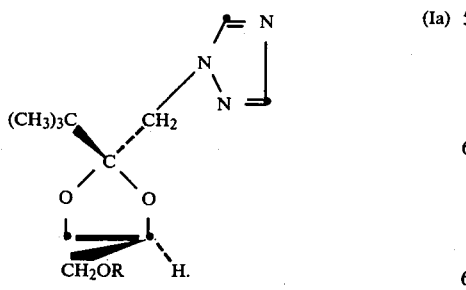

The configuration Ia is to be denoted, here and in the following, as the "trans" isomer.

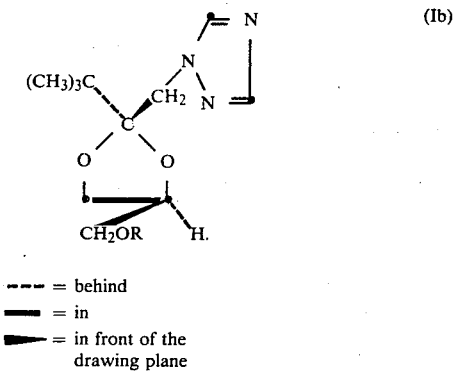

--- = behind
—— = in
▶— = in front of the drawing plane

The configuration Ib is accordingly to be denoted as the "cis" isomer. The separation of the two diastereoisomers Ia and Ib can be performed for example by fractional crystallisation or by chromatography (thin-layer, thick-layer, column, liquid-high-pressure chromatography, and so forth). The two isomers exhibit in part differing microbicidal activity. The diastereoisomeric mixtures are in general used for practical purposes. The characterisation of the two configurations can be effected for example by means of NMR spectroscopic methods. The invention embraces all isomeric compounds and the salts and metal complexes thereof.

The starting compounds II, IV, V and VI are known, and can be produced by methods known per se.

1-(β-Aryl)-ethylimidazolyl ketals, wherein aryl is substituted phenyl or naphthyl, are cited in the following references as fungicides and bactericides: U.S. Pat. Specifications Nos. 3,575,999, 3,936,470, 4,101,664, 4,101,666 and 4,156,008.

It has been found that compounds of the formula I surprisingly exhibit a very favourable microbicidal spectrum for practical requirements. They can be used for example to protect cultivated plants.

The main field of application for compounds of the formula I is the combating of harmful microorganisms, particularly phytopathogenic fungi. The compounds of the formula I thus have for practical purposes a very favourable curative, preventive and systemic action for the protection of cultivated plants, without these being impaired as a result of undesirable side-effects. Cultivated plants within the scope of the present invention are for example: cereals (wheat, barley, rye, oats and rice); beet: (sugar beet and fodder beet); pomaceous fruit, stone fruit and soft fruit: (apples, pears, plums, peaches, almonds, cherries, strawberries, rasberries and blackberries); legumes: (beans, lentils, peas and soyabean); oil plants: (rape, mustard, poppy, olives, sunflowers, coco, castor-oil plants, cocoa and groundnuts); Cucurbitacea: (pumpkins, cucumbers and melons); fibre plants: (cotton, flax, hemp and jute); citrus fruits: (oranges, lemons, grapefruit and mandarins); varieties of vegetables: (spinach, lettuce, asparagus, varieties of cabbage, carrots, onions, tomatoes, potatoes and paprika); or plants such as maize, tobacco, nuts, coffee, sugar beet, tea, grapevines, hops, bananas and natural rubber plants; and also ornamental plants.

Microorganisms occurring on plants or on parts of plants (fruit, blossom, foliage, stalks, tubers or roots) of the said crops and of related cultivated crops can be inhibited or destroyed with the active substances of the formula I, and also parts of plants subsequently growing remain preserved from such microorganisms. The active substances are effective against the phytopathogenic fungi belonging to the following classes: Ascomycetes (for example Venturia and Erysiphaceae); Basidiomycetes, such as in particular rust fungi (for example Puccinia); Fungi imperfecti (for example Moniliales, and so forth, Botrytis, and Cercospora pathogens belonging to the Dematiaceae family). Furthermore, the compounds of the formula I have a systemic action. They can also be used as dressing agents for treating seed (fruits, tubers and grain), and plant cuttings to protect them from fungus infections, and also against phytopathogenic fungi occurring in the soil.

The invention relates therefore also to the use of the compounds of the formula I for combating phytopathogenic microorganisms and/or for preventing infection on plants.

Compared with the cited compounds, the ketals of the formula I of the present invention have an improved microbicidal spectrum for the protection of cultivated plants, and are distinguished, when applied in the customary amounts for protecting plants, by the absence of phytotoxicity, so that they protect the cultivated plants against harmful microorganisms without damaging the plants.

For combating these microorganisms, the compounds of the formula I can be used on their own or together with suitable carriers and/or other additives. Suitable carriers and additives can be solid or liquid and they correspond to the substances common in formulation practice, such as natural or regenerated mineral substances, solvents, dispersing agents, wetting agents, adhesives, thickeners, binding agents and/or fertilisers. Active substances of the formula I can be used also in admixture, for example with pesticidal preparations or with preparations which improve the growth of plants. The Examples which follow serve to further illustrate the nature of compositions of this type. The content of active ingredient in commercial preparations is between 0.0001 and 90%.

Temperature values in the following Examples are given in degrees Centigrade, and 'parts' and percentages are always by weight.

PRODUCTION EXAMPLES

EXAMPLE 1

(a) Production of a starting product

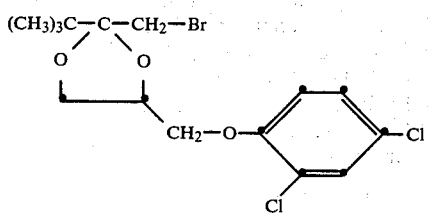

2-Tert-butyl-2-bromomethyl-4-(2,4-dichlorophenoxy)-methyl-1,3-dioxolane 0.2 g of p-toluenesulfonic acid is added to 27 g of bromopinacolin and 37 g of glycerin-1-(2,4-dichlorophenyl)-ether in a mixture of of 200 ml of toluene and 50 ml of n-butanol, and the whole is refluxed for 48 hours with use of a water separator. The reaction solution is cooled to room temperature, and is then washed twice with sodium hydrogen carbonate and once with water; it is subsequently dried over sodium sulfate and concentrated by evaporation. The formed colourless oil crystallises after the addition of 10 ml of methanol; yield 57 g; m.p. 80°-83°.

(b) Preparation of the final product

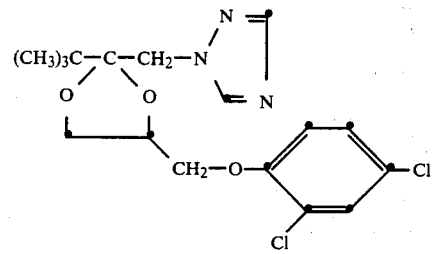

2-Tert-butyl-2-(1H-1,2,4-triazol-1-yl)-methyl-4-(2,4-dichlorophenoxy)-methyl-1,3-dioxolane 3.5 g of 1,2,4-triazole potassium salt in 100 ml of absolute dimethylformamide are heated to 100°. To the hot solution are added dropwise 9 g of 2-tert-butyl-2-bromomethyl-4-(2,4-dichlorophenoxy)-methyl-1,3-dioxolane dissolved in 50 ml of absolute dimethylformamide. The reaction mixture is subsequently stirred for 24 hours at 130°; the solvent is then removed in vacuo and the residue is extracted with diethyl ether; the ether phase is washed with water and dried over sodium sulfate. The yield after concentration by evaporation is 7 g of a viscous oil which, after the addition of n-hexane, crystallises to give the cis isomer, m.p. 113°-114°. The trans isomer, m.p. 73°-74°, can be obtained from the mother liquor.

The following final products (except where specifically stated, these are diastereoisomeric mixtures of differing mixture ratios which have not been further analysed) of the formula I can be produced in an analogous manner.

TABLE 1

| | Compounds of the formula I | | |
|---|---|---|---|
| No. | R | Salt or complex | Physical data |
| 1 | $C_6H_5$— | — | m.p. 80–82° |
| 2 | 2-$CH_3$—4-$CH_3$—$C_6H_3$— | — | m.p. 113–115° |
| 3 | 4-tert. $C_4H_9$—$C_6H_4$— | — | m.p. 98–100° |
| 4 | 4-$C_6H_5$—$C_6H_4$— | — | m.p. 110–114° |
| 5 | 3-$CF_3$—$C_6H_4$—(trans) | — | m.p. 96–97° |
| 6 | 3-$CF_3$—$C_6H_4$—(cis) | — | viscous oil |
| 7 | 3-$CF_3$—$C_6H_4$—(cis) | $CuCl_2$ | m.p. 228–230° |
| 8 | 4-F—$C_6H_4$— | — | m.p. 50–59° |
| 9 | 4-F—$C_6H_4$— | $HNO_3$ | m.p. 130–132° |
| 10 | 4-Cl—$C_6H_4$— | $HNO_3$ | m.p. 126–129° |
| 11 | 4-Br—$C_6H_4$— | — | m.p. 109–111° |
| 12 | 2-Cl—4-Cl—$C_6H_3$— | — | m.p. 69–97° |
| 13 | 2-Cl—4-Cl—$C_6H_3$— | HCl | m.p. 155–160° |
| 14 | 2-Cl—4-Cl—$C_6H_3$—(trans) | — | m.p. 73–74° |
| 15 | 2-Cl—4-Cl—$C_6H_3$—(cis) | — | m.p. 113–114° |
| 16 | 2-Cl—6-Cl—$C_6H_3$— | — | m.p. 78–81° |
| 17 | 2-Cl—5-Cl—$C_6H_3$— | — | m.p. 133–134° |
| 18 | 2-$CH_3$—4-Cl—$C_6H_3$— | — | viscous oil |
| 19 | 2-F—$C_6H_4$— | — | viscous oil |
| 20 | 3-F—$C_6H_4$— | — | highly viscous |
| 21 | 2-Cl—$C_6H_4$— | — | viscous oil |
| 22 | 3-Cl—$C_6H_4$— | — | |
| 23 | 3-Br—$C_6H_4$— | — | viscous oil |
| 24 | 2-Cl—3-Cl—$C_6H_3$— | — | |
| 25 | 3-Cl—5-Cl—$C_6H_3$— | — | viscous oil |
| 26 | 3-Cl—4-Cl—$C_6H_3$— | — | m.p. 86–91° |
| 27 | 3-$OCH_3$—$C_6H_4$— | — | viscous oil |
| 28 | 3-$CH_3$—4-Cl—$C_6H_3$— | — | viscous oil |
| 29 | 2-$CH_3$—4-Cl—6-Cl—$C_6H_2$— | — | Viscous oil |
| 30 | 3,4-(—O—$CH_2$—O—)-$C_6H_3$— | — | viscous oil |

TABLE 1-continued

| No. | R | Salt or complex | Physical data |
|---|---|---|---|
| 31 | 2-Br—4-Cl—$C_6H_3$ | — | viscous oil |
| 32 | 3-$C_2H_5$—$C_6H_4$ | — | viscous oil |
| 33 | 2-$C_2H_5$—$C_6H_4$ | — | viscous oil |
| 34 | 4-$C_2H_5$—$C_6H_4$ | — | m.p. 78–84° |
| 35 | 3-$CH_3$—4-Cl—5-$CH_3$—$C_6H_2$ | — | m.p. 140–142° |
| 36 | 2-$OCH_3$—$C_6H_4$ | — | viscous oil |
| 37 | 2-$CH_3$—3-$CH_3$—$C_6H_3$ | — | viscous oil |
| 38 | 2-$CH_3$—3-$CH_3$—6-$CH_3$—$C_6H_2$ | — | viscous oil |
| 39 | 2-Br—$C_6H_4$ | — | viscous oil |
| 40 | 2-tert.-Butyl—5-$CH_3$—$C_6H_3$ | — | viscous oil |
| 41 | 2-$OCH_3$—6-$OCH_3$—$C_6H_3$ | — | viscous oil |
| 42 | 2-tert.-Butyl—$C_6H_4$ | — | viscous oil |

The compounds of the formula I can be applied in the following forms:

FORMULATION EXAMPLES

EXAMPLE 2: SOLID PREPARATIONS

Dusts and scattering agents contain in general up to 100% of active substance. A 5% dust can consist for example of 5 parts of the active substance and 95 parts of an additive, such as talcum, or of 5 parts of active substance, 4 parts of highly dispersed silicic acid and 91 parts of talcum. In addition to these, other mixtures with carriers and additives of this type and of other types customary in formulation practice are possible. These dusts are produced by mixing and grinding the active substances with the carriers and additives, and they can be dusted on in this form.

Granulates, such as coated granules, impregnated granules and homogeneous granules, and also pellets, usually contain 1 to 80% of active substance. Thus, a 5% granulate can be composed for example of 5 parts of active substance, 0.25 part of epoxidised vegetable oil, 0.25 part of cetyl polyglycol ether, 3.50 parts of polyethylene glycol and 91 parts of kaolin (preferred particle size: 0.3–0.8 mm). The granulates can be prepared as follows:

The active substance is mixed with epoxidised vegetable oil, and the mixture is dissolved in 6 parts of acetone, whereupon the polyethylene glycol and cetyl polyglycol ether are added. The solution thus obtained is sprayed onto kaolin, and the acetone is subsequently evaporated off in vacuo. A microgranulate of this type is advantageously used for combating soil fungi.

EXAMPLE 3: LIQUID PREPARATIONS

A distinction is general made between active-substance concentrates which are dispersible or soluble in water and aerosols. Water-dispersible concentrates of active substance include for example wettable powders and pastes, which usually contain in the commercial packing 25–90% of active substance, and in ready-for-use solutions 0.01 to 15% of active substance. Emulsion concentrates contain 10 to 50% of active substance, and solution concentrates contain in the ready-for-use solution 0.0001 to 20% of active substance. A 70% wettable powder can thus consist of for example 70 parts of active substance, 5 parts of sodium dibutylnaphthyl sulfonate, 3 parts of naphthalenesulfonic acid/phenolsulfonic acid/formaldehyde condensate (in the mixture ratio of 3:2:1), 10 parts of kaolin and 12 parts of chalk, for example Champagne chalk. A 40% wettable powder can consist for example of the following substances: 40 parts of active substance, 5 parts of sodium lignin sulfonate, 1 part of sodium dibutylnaphthalene sulfonate and 54 parts of silicic acid. A 25% wettable powder can be prepared in various ways. It can thus be composed for example of: 25 parts of active substance, 4.5 parts of calcium lignin sulfonate, 1.9 parts of chalk, for example Champagne chalk/hydroxyethylene cellulose mixture (1:1), 1.5 parts of sodium dibutylnaphthylsulfonate, 19.5 parts of silicic acid, 19.5 parts of chalk, for example Champagne chalk, and 28.1 parts of kaolin. A 25% wettable powder can consist for example of 25 parts of active substance, 2.5 parts of isooctylphenoxypolyoxyethylene-ethanol, 1.7 parts of [Champagne]-chalk/hydroxyethyl cellulose mixture (1:1), 8.3 parts of sodium silicate, 16.5 parts of kieselguhr and 46 parts of kaolin. A 10% wettable powder can be produced for example from 10 parts of active substance, 3 parts of a mixture of sodium salts of saturated fatty alcohol sulfonates, 5 parts of naphthalenesulfonic acid/formaldehyde condensate and 82 parts of kaolin. Other wettable powders can be mixtures of 5 to 30% of active substance together with 5 parts of an absorptive carrier material, such as silicic acid, 55 to 80 parts of a carrier such as kaolin and of a dispersing agent mixture consisting of 5 parts of sodium aryl sulfonate and of 5 parts of an alkylarylpolyglycol ether. A 25% emulsion concentrate can contain for example the following emulsifiable substances: 25 parts of active substance, 2.5 parts of epoxidised vegetable oil, 10 parts of an alkylaryl sulfonate/fatty alcohol polyglycol ether mixture, 5 parts of dimethylformamide and 57.5 parts of xylene.

Emulsions of the required application concentration can be produced from concentrates of the described types by dilution with water, and these emulsions are particularly suitable for leaf application. In addition, other wettable powders having different mixture ratios or containing other carriers and additives common in formulation practice can be produced. The active substances are intimately mixed, in appropriate mixers, with the additives mentioned, and the mixture is then ground in suitable mills and rollers. There are obtained wettable powders which have excellent wetting and suspension properties, which can be diluted with water to give suspensions of the desired concentration, and which can be used in particular for leaf application. Compositions of this kind also form part of the subject matter of the present invention.

Compositions, which have been formulated in the above described manner and which contain a compound of the formula I (for example compound No. 1, 4, 5, 7, 9, 10, 11, 12, 13, 14, 26 or 34) can be used very successfully for combating phytopathogenic microorganisms. Also other compounds from Table I can be used with an equally high or similar degree of success.

BIOLOGICAL EXAMPLES

The spray liquors used in the following Examples have been formulated in the manner described above.

EXAMPLE 4: ACTION AGAINST *CERCOSPORA ARACHIDICOLA* ON GROUNDNUT PLANTS

Three-week old groundnut plants were sprayed with a spray liquor produced from wettable powder of the active substance (0.02% of active substance). The treated plants were dusted after about 12 hours with a conidiospore suspension of the fungus. The infested plants were then incubated for about 24 hours with 90% relative humidity, and were subsequently transferred to a greenhouse at about 22° C. The amount of fungus infection was assessed after 12 days.

In comparison with the untreated control plants, the plants which had been treated with active substances of the formula I displayed only a slight amount of fungus infection or virtually none at all.

The compounds Nos. 10 and 13 prevent fungus infection, even at a concentration of only 0.002%.

EXAMPLE 5: ACTION AGAINST *PUCCINIA GRAMINIS* ON WHEAT (a) Residual-protective action Six days after being sown, wheat plants were sprayed with a spray liquor prepared from wettable powder of the active substance (0.06% of active substance). After 24 hours, the treated plants were infested with a uredospore suspension of the fungus. After an incubation time of 48 hours at about 20° C. with 95–100% relative humidity, the infested plants were kept in a greenhouse at about 22° C. An assessment of the development of rust pustules was made 12 days after infestation.

The compounds Nos. 1, 4, 5, 11, 12, 26 and 34 reduced the rust-pustule infection to less than 10% compared with that occurring on untreated control plants (100% rust-pustule infection).

The compounds Nos. 4 and 12 prevented fungus infection even at a concentration of active substance of only 0.002%.

(b) Systemic action

A spray liquor produced from wettable powder of the active substance (0.006% of active substance, relative to the volume of soil) was applied to the soil of wheat plants 5 days after sowing. After 3 days, the treated plants were infested with a uredospore suspension of the fungus. After incubation for 48 hours at about 20° C. with 95–100% relative humidity, the infested plants were kept in a greenhouse at about 22° C. An assessment of the development of rust pustules was made 12 days after infestation. Compounds of the formula I exhibited a high level of effectiveness. The compounds Nos. 1, 7 and 11 prevented the spread of the disease completely.

EXAMPLE 6: RESIDUAL PROTECTIVE ACTION AGAINST *VENTURIA INAEQUALIS* ON APPLE SHOOTS

Apple seedlings having 10–20 cm long fresh shoots were sprayed with a spray liquor prepared from wettable powder of the active substance (0.06% of active substance). The treated plants were sprayed after 24 hours with a conidiospore suspension of the fungus. The plants were then incubated for 5 days with 90–100% relative humidity, and for a further 10 days they were kept at 20°–24° C. in a greenhouse. The extent of scab infection was assessed 15 days after infestation. The occurrence of the disease was prevented, even at a concentration of active ingredient of 0.02%, by, inter alia, compounds Nos. 5, 11, 12 and 26.

EXAMPLE 7: ACTION AGAINST *ERYSIPHE GRAMINIS* ON BARLEY (a) Residual protective action Barley plants about 8 cm high were sprayed with a spray liquor prepared from wettable powder of the active substance (0.02% of active substance). The treated plants were dusted after 3–4 hours with conidiospores of the fungus. The infested barley plants were transferred to a greenhouse at about 22° C., and the fungus infection was assessed after 10 days.

(b) Systemic action

A spray liquor produced from wettable powder of the active substance (0.006% of active substance, relative to the volume of soil) was applied to the soil of barley plants about 8 cm in height. Care was taken to ensure that the spray liquor did not come into contact with the parts of the plants above the soil. The treated plants were dusted after 48 hours with conidiospores of the fungus. The infested barley plants were kept in a greenhouse at about 22° C., and the fungus infection was assessed after 10 days. In the tests (a) and (b), the compounds of the formula I exhibited a total action (fungus infection completely prevented). Even at a dilution concentration of only 0.002%, the compounds 1, 5, 11, 12, 13, 14, 26 and 34 were completely effective in test (a). This effect at a concentration of 0.002% was exhibited also in test (b) by, amongst others, compounds Nos. 5, 11, 12 and 14.

EXAMPLE 8: ACTION AGAINST *BOTRYTIS CINEREA* ON APPLES

Artificially damaged apples were treated by applying drops of spray liquor, prepared from wettable powder of the active substance, to the damaged areas on the apples. The treated fruit was subsequently inoculated with a spore suspension of *Botrytis cinerea*, and then incubated for one week at about 20° C. with high relative humidity. An assessment was made by counting the decayed damaged areas, and deducing from that the fungicidal action. Compared with the fungus infection on untreated control fruit (100% infection), that on the treated fruit had been prevented virtually completely by, amongst others, compounds Nos. 9 and 10.

What is claimed is:

1. A compound selected from the group consisting of a 1,3-dioxolane of the formula:

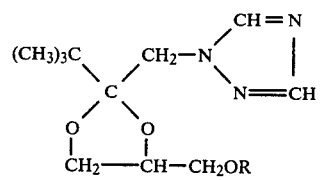

wherein R is phenyl or phenyl substituted with from one to four substituents selected from the group consisting of chloro and trifluoromethyl, the nonphytotoxic acid addition salts thereof and the nonphytotoxic metal complexes thereof.

2. A compound according to claim 1 wherein R is trifluoromethylphenyl or dichlorophenyl.

3. The compounds according to claim 2 wherein R is 3-trifluoromethylphenyl.

4. The compound according to claim 2 wherein R is 2,4-dichlorophenyl.

5. The compound according to claim 2 wherein R is 3,4-dichlorophenyl.

6. A composition for combatting microorganisms which comprises an effective amount of a compound according to claim 1 and an inert carrier therefor.

7. A composition for combatting microorganisms which comprises an effective amount of the compound according to claim 3 and an inert carrier therefor.

8. A composition for combatting microorganisms which comprises an effective amount of the compound according to claim 4 and an inert carrier therefor.

9. A composition for combatting microorganisms which comprises an effective amount of the compound according to claim 5 and an inert carrier therefor.

10. The method of combatting microorganisms which comprises applying an effective amount of a compound according to claim 1 to the locus of said microorganism.

11. The method of combatting microorganisms which comprises applying an effective amount of the compound according to claim 3 to the locus of said microorganism.

12. The method of combatting microorganisms which comprises applying an effective amount of the compound according to claim 4 to the locus of said microorganism.

13. The method of combatting microorganisms which comprises applying an effective amount of the compound according to claim 5 to the locus of said microorganism.

* * * * *